US006976997B2

(12) United States Patent
Noolandi et al.

(10) Patent No.: US 6,976,997 B2
(45) Date of Patent: Dec. 20, 2005

(54) ARTIFICIAL CORNEA

(75) Inventors: Jaan Noolandi, Palo Alto, CA (US); Christopher Ta, Palo Alto, CA (US); Philip Huie, Jr., Cupertino, CA (US); Alan J. Smith, Redwood City, CA (US); Robert Waymouth, Stanford, CA (US); Mark Blumenkranz, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 10/465,040

(22) Filed: Jun. 18, 2003

(65) Prior Publication Data

US 2004/0049268 A1 Mar. 11, 2004

Related U.S. Application Data

(60) Provisional application No. 60/390,060, filed on Jun. 18, 2002.

(51) Int. Cl.[7] .............................................. A61F 2/14
(52) U.S. Cl. ..................................... 623/5.14; 623/5.16
(58) Field of Search ............................. 623/5.14, 5.11, 623/5.15, 5.16

(56) References Cited

U.S. PATENT DOCUMENTS

| | | | | |
|---|---|---|---|---|
| 4,551,486 A | * | 11/1985 | Tateosian et al. ............ 523/212 |
| 4,772,283 A | | 9/1988 | White ............................ 623/5 |
| 4,932,968 A | * | 6/1990 | Caldwell et al. ............ 623/6.37 |
| 5,135,297 A | * | 8/1992 | Valint, Jr. ................. 351/160 R |
| 5,171,318 A | * | 12/1992 | Gibson et al. ............... 623/5.16 |
| 5,282,851 A | * | 2/1994 | Jacob-LaBarre ............ 623/6.56 |
| 5,300,115 A | * | 4/1994 | Py ............................. 623/5.15 |
| 5,300,116 A | * | 4/1994 | Chirila et al. ............... 623/5.14 |
| 5,489,301 A | * | 2/1996 | Barber ........................ 623/5.11 |
| 5,509,968 A | | 4/1996 | Carr ................................ 134/1 |
| 2002/0007217 A1 | * | 1/2002 | Jacob et al. ................ 623/5.16 |

OTHER PUBLICATIONS

Chirila, T.V., An overview of the development of artificial corneas with porous skirts and the use of pHEMA for such an application, Biomaterials, 22, 3311-3317 (2001) (Dec. 15, 2001).

Hicks et al., "Development and clinical assessment of an artificial cornea", Prog Retin Eye Res., 19, 149-170 (2000).

Vijay asekaran et al., "Cell viability and inflammatory response in hydrogel sponges implanted in the rabbit cornea", Biomaterials, 19, 2255-2267 (1998).

(Continued)

*Primary Examiner*—Paul B. Prebilic
(74) *Attorney, Agent, or Firm*—Lumen Intellectual Property Services, Inc.

(57) ABSTRACT

The invention provides implants suitable for use as an artificial cornea, and methods for making and using such implants. Artificial corneas having features of the invention may be two-phase artificial corneas, or may be three phase artificial corneas. These artificial corneas have a flexible, optically clear central core and a hydrophilic, porous skirt, both of which are biocompatible and allow for tissue integration. A three-phase artificial cornea will further have an interface region between the core and skirt. The artificial corneas have a high degree of ocular tolerance, and allow for tissue integration into the skirt and for epithelial cell growth over the surface of the prosthesis. The use of biocompatible material avoids the risk of disease transmission inherent with corneal transplants, and acts to minimize post-operative inflammation and so to reduce the chance or severity of tissue necrosis following implantation of the synthetic cornea onto a host eye.

14 Claims, 5 Drawing Sheets

OTHER PUBLICATIONS

Hicks et al., Implantation of pHEMA keratoprostheses after alkali burns in rabbit eyes, Cornea, 17, 301-308 (1998).

Hicks et al., "Clinical results of implantation of the chirila keratoprosthesis in rabbits", Br J Opthamol, 82, 18-25 (1998).

Vijayasekaran et al., "Histologic evaluation during healing of hydrogel core-and-skirt keratoprostheses in the rabbit eye", Cornea 16, 52-59 (1997).

Hicks et al., "Keratoprosthesis: preliminary results of an artificial corneal button as a full-thickness implant in the rabbit model", Aust N Z J Ophthamol, 24, 297-303 (1996).

Crawford et al., "Preliminary evaluation of hydrogel core-and-skirt keratoprosthesis in the rabbit cornea", J. Refract Surg. 12, 525-529 (1996).

Crawford et al., "Tissue interaction with hydrogel sponges implanted in the rabbit cornea", Cornea, 12, 348-357 (1993).

Sanderman et al., Novel materials to enhance keratoprosthesis integration, Br J. Ophthalmol 84, 640-644 (2000).

Dropcova et al., "A standard strain of human ocular keratocytes", Ophthalmic Res. 31, 33-41 (1999).

Kim et al., "Effect of Poly(ethylene glycol) graft polymerization of poly(methyl methacrylate) on cell adhesion", J. Cataract Refract. Surg., 27, 766-744 (2001).

Hawker, "Accurate structural control and block formation in the living polymerization of 1,3-dienes by nitroxide-mediated procedures",macromolecules 33, 363-370 (2000).

Kirkham, et al., "The keratoprosthesis: Improved biocompatibility through design and surface modification", Ophthalmic Surgery, 22, 455-461 (1991).

Low, M.G., "Glycosyl-phosphatidylinositol: A versatile anchor for cell surface proteins", The FASEB Journal, 3, 1600-1608 (1989).

Fu, et al., Protein stability in controlled release systems: Nature Biotechnology, 18, 24-25 (2000).

Mondargent et al., "Toward new biomaterials", Infect. Control Hosp. Epidemiol., 21, 404-410 (2000).

Trinkaus-Randall V. et al., "In vivo fibroplasia of a porous polymer in a cornea", Invest Ophthamol Vis Sci 32, 3245-3251 (1991).

Trinkaus-Randall et al., "In vitro evaluation of fibroplasia in a porous polymer," Invest Opthalmol Vis Sci 31, 1321-6 (1990).

Legeais et al., "A second generation of biointegrable keratoprosthesis. First in vivo evaluation" (abstract), Invest Ophthalmol Vis Sci 37 (suppl) 37,1450 (1996).

Legeais et al., "Advances in artificial corneas" (abstract), Invest Ophthalmol Vis Sci 37 (suppl) 36, 1466 (1995).

Kain The development of the silicon-carbon keratoprosthesis. Refract corneal surg 9,209-10.

Chirila TV, Constable IJ, Crawford GJ, et al., "Poly (2-hydroxyethy methacrylate) sponges as implant materials: in vivo and in vitro evaluation of cellular invasion", Biomaterials 14, 26-28 (1993).

Trinikauss-Randall et al., "Development of a biopolymeric keratoprosthetic material" Invest Ophthalmol Vis Sci 29, 393-400 (1988).

Hicks et al., "Keratoprostheses: Advancing toward a true artificial cornea" Survey of Ophthalmology 42, 175-189 (1997).

Malinda et al., "Thymosin B4 accelerates wound healing" Journal of Investigative Dermatology, 113, 364-368 (1999).

Desai et al., "Nanopore technology for biomedical applications", Biomedical microdevices, , 11-40 (1999) may be used to prepare surfaces of artificial corneas.

McGrady et al., "Specific and charge interactions mediate collagen recognition by oral lactobacilli", J. Dent. Res., 74, 649-657 (1995).

Abulencia et al., "Comparative antiplatelet efficacy of a novel, Nonpeptide GPIIb/IIIa Antagonist (XV454) and Adciximab (c7E3) in flow models of thrombosis", Arterioslcer Thromb. Vasc. Biol., 21, 149-156 (2001).

Margel et al., "Peptide, protein and cellular interactions with self-assembled monolayer model surfaces", J. Biomed, Mater, Res., 27, 1463-1476 (1993).

Zheng et al., "Modification of materials formed from poly (L-lactic acid) to enable covalent binding of biopolymers: Application to high-density three-dimensional cell culture in foams with attached collagen", In Vitro Cell Dev. Biol. Anim., 34, 679-684 (1998).

Tjia et al., "Substrate-absorbed collagen and cell secreted fibronectin concertedly induce cell migration on poly (lactide-glycolide) Substrates", Biomaterials, 20, 2223-2233 (1999).

Trinkauss-Randall, "Cornea", Ch. 35 in Principles of Tissue Engineering, 2$^{nd}$ ed., Academic Press (2000).

* cited by examiner

ARTIFICIAL CORNEA

CROSS-REFERENCE TO RELATED APPLICATIONS

This application is cross-referenced to and claims priority from U.S. Provisional Application No. 60/390,060 filed Jun. 18, 2002 which is hereby incorporated by reference.

FIELD OF THE INVENTION

The present invention relates generally to the field of treatment of eye disorders. In particular, the present invention relates to disorders that require replacement of the cornea.

BACKGROUND

The cornea provides protection for the intraocular contents of the eye and to refract and focus light onto the retina. Many diseases can lead to opacity of the cornea, resulting in blindness. These include trauma, infections, inflammation, previous ocular surgery, and genetic conditions. It is estimated that there are approximately 8 to 10 million people worldwide who are blind due to corneal diseases and that would benefit from a corneal transplant. The current treatment for opacity of the cornea is a penetrating keratoplasty (cornea transplant), in which a damaged or diseased cornea is replaced by a cornea taken from a donor eye. The replacement corneal tissue has to be obtained from a deceased donor, and preserved until the time of transplantation. The tissue has to be harvested within 12 hours of death, and used within approximately seven days. The success rate depends on the existing underlying condition of the eye. The major limitations of penetrating keratoplasty in underdeveloped and developing countries are tissue availability and cost. Due to cultural and religious reasons in these countries, and limited resources to develop an eye tissue bank, cornea transplant has not been feasible.

Even in developed countries in which corneal transplants are available, there are many potential complications with penetrating keratoplasty that can limit vision, such as severe astigmatism, corneal graft rejection and failure, glaucoma, and infections resulting in loss of vision. In addition, many corneal diseases cannot be treated with penetrating keratoplasty. These include patients with chemical burns, Stevens-Johnson disease, trachoma, severe dry eyes, and recurrent corneal graft failure.

Although an artificial cornea would solve the problem of corneal tissue availability and other problems, prior art attempts have been unsuccessful to develop an artificial cornea. One challenge of developing an artificial cornea is to design and manufacture a structure that is optically clear centrally and biocompatible peripherally that would allow for cellular integration has proven difficult in practice. Artificial corneas that have been implanted in patients have had severe complications, such as endophthalmitis (intraocular infections), extrusion, glaucoma (uncontrolled elevated intraocular pressure), epithelial downgrowth, uveitis (intraocular inflammation) and tissue necrosis. These complications may be partly due to poor tissue adhesion between the keratoprothesis and the recipient tissue, resulting in severe irreversible loss of vision.

A keratoprosthesis designed by Chirila et al. is one recent development in the field (see, e.g., Chirila, T. V. "An Overview of the Development of Artificial Corneas With Porous Skirts and the Use of pHEMA for Such an Application", Biomaterials, 22, 3311–3317 (2001); Hicks et al., "Development and clinical assessment of an artificial cornea", Prog Retin Eye Res., 19, 149–170 (2000); Vijayasekaran et al., "Cell viability and inflammatory response in hydrogel sponges implanted in the rabbit cornea", Biomaterials, 19, 2255–2267 (1998); Hicks et al. "Implantation of pHEMA keratoprostheses after alkali burns in rabbit eyes", Cornea, 17, 301–308 (1998); Hicks et al. "Clinical results of implantation of the Chirila keratoprosthesis in rabbits", Br J Ophthalmol. 82, 18–25 (1998); Vijayasekaran et al. "Histologic evaluation during healing of hydrogel core-and-skirt keratoprostheses in the rabbit eye", Cornea, 16, 52–59 (1997); Hicks, et al. "Keratoprosthesis: preliminary results of an artificial corneal button as a full-thickness implant in the rabbit model", Aust N Z J Ophthalmol. 24, 297–303 (1996); Crawford et al. "Preliminary evaluation of hydrogel core-and-skirt keratoprosthesis in the rabbit cornea", J Refract Surg. 12, 525–529 (1996); Crawford et al. "Tissue interaction with hydrogel sponges implanted in the rabbit cornea", Cornea, 12, 348–357 (1993).

A keraprosthesis as made by Chirila et al. has the feature that it is formed from a single polymer, poly(2 hydroxyethyl methacrylate) or pHEMA. This ensures that there is an intimate coupling between the core and the skirt. This polymer is a biocompatible polymer. The use of biocompatible materials may be helpful in overcoming the problem of extrusion of the keratoprostheses often found with artificial corneas (see, e.g., Chirila, T. V. "An Overview of the Development of Artificial Corneas With Porous Skirts and the Use of pHEMA for Such an Application", Biomaterials, 22, 3311–3317 (2001)).

In addition, pHEMA is hydrophilic, so that biological material can penetrate the structure. The Chirila et al. keraprosthesis is made by polymerizing the pHEMA under different conditions for the core and the skirt (Chirila, T. V. "An Overview of the Development of Artificial Corneas With Porous Skirts and the Use of pHEMA for Such an Application", Biomaterials, 22, 3311–3317 (2001)). A hard transparent core material results from using 35% water in the initial mixture, whereas 45% or more water results in a spongy material. The skirt is polymerized first using a higher concentration of water and the hard core is then polymerized by reducing the water concentration.

Another group has found that incorporation of the hydrophobic monomer phenoxyethyl methacrylate (PEM) in the free radical polymerization of the pHEMA hydrogel appears to enhance cell adhesion and growth onto the hydrogel (Sandemann et al. "Novel Materials to Enhance Keratoprosthesis Integration", Br. J. Ophthalmol., 84, 640–644 (2000)). The enhancement of cell spreading may result from the moderation of pHEMA based hydrophilicity by the incorporation of aromatic monomers (Dropcova et al. "A Standard Strain of Human Ocular Keratocytes", Ophthalmic Res. 31, 33–41 (1999)).

Artificial corneas that have been developed over the past 40 to 50 years have not been successful and had serious complications, including endophthalmitis (intraocular infection), extrusion, and glaucoma resulting in complete and irreversible loss of vision. This is due, in part, to the lack of biocompatibility, resulting in chronic inflammation and tissue necrosis. A corneal prosthesis as described by Chirila et al. is composed of pHEMA that appears to be biocompatible with some measure of cellular integration. However, improvements on both the materials and design of a keratoprothesis are necessary to further enhance tissue integration.

Accordingly, there is need for an artificial cornea that is biocompatible and that reduces serious complications in place in a recipient eye.

SUMMARY OF THE INVENTION

The invention provides implants suitable for use as an artificial cornea, and methods for making and using such implants. Artificial corneal implants embodying features of the invention include multiphase artificial corneas having a clear core and a periphery constituting a different phase in construction and/or materials. In one embodiment, a two-phase artificial cornea is provided that is clear centrally, and has a biocompatible, hydrophilic and porous skirt in the periphery. In another embodiment, a three-phase artificial cornea is provided that is clear centrally, has a biocompatible, hydrophilic and porous skirt in the periphery, and a core/skirt interface (such as a polymer brush linking region) between the core and skirt regions. The hydrophilic, porous skirt is configured to aid tissue integration into the skirt and to aid in the growth of epithelial cells over the surface of the artificial cornea. A core/skirt interface is configured to improve the mechanical properties of an artificial cornea and to add other desirable features to an artificial cornea. Artificial corneas having features of the invention are thus core/skirt constructs, optionally including a core/skirt interface as a linking region between the core and skirt, that are easy to suture onto the recipient bed, and have adequate mechanical strength to withstand the mechanical stresses normally encountered by a cornea in situ.

The implants of the present invention are configured to, and include materials, which promote cellular ingrowth as well as epithelialization of the surface of the artificial cornea (also termed "keraprosthesis"). Hybrid synthetic/biomolecular artificial corneas embodying features of the invention have a high degree of ocular tolerance, and are composed of a flexible central core and a porous skirt, both of which are biocompatible and allow for tissue integration. The use of biocompatible material avoids the risk of disease transmission inherent with corneal transplants, and acts to minimize post-operative inflammation and so to reduce the chance or severity of tissue necrosis following implantation of the synthetic cornea onto a host eye.

Implants embodying features of the invention are made of biocompatible materials, and have a clear central optic core. The edge of the core is chemically functionalized to aid the attachment of a skirt to the core by chemical bonding. The skirt is also chemically functionalized to allow the covalent attachment of biocompatible materials such as collagen to the core/skirt construct. This construction allows keratocytes (corneal cells) to integrate and produce extracellular matrix within the pores of the artificial cornea, with epithelial cells covering the surface, while remaining optically clear centrally. Antibiotics and cell growth promoters may also be attached to the core/skirt construct. These elements aid in reducing inflammation and rejection of an artificial cornea, and promote epithelial growth and integration of cells. Growth and integration of keratocytes and other cells into the implants is effective to provide a watertight junction between the artificial cornea and the host tissue bed, preventing endophthalmitis and extrusion. Growth and integration of cells is enhanced in artificial corneas embodying features of the invention by the use of materials that allow maximum number of keratocytes to integrate into the artificial cornea, by producing uniform pore size in the materials, by providing a biocompatible environment (such as polymer coated with collagen) and by using proteins and cytokines that can initiate cell migration and adhesion. The invention also provides methods for assessing the performance of materials and compositions used to make artificial corneas and of artificial cornea implants themselves.

The artificial cornea embodying features of the invention could be further developed such that a surface biocompatible material (e.g. pHEMA) is chemically modified to promote epithelialization and tissue integration at one site of the material (preferably the anterior site). Examples of chemical methods are for example, but not limited to, TEMPO oxidation and bleach oxidation.

Artificial cornea implants embodying features of the invention provide the advantage of a higher degree of ocular tolerance, improved biocompatibility, increased mechanical strength, ease of implantation, elimination of the risk of disease transmission from transplanted tissue, and better management of post-operative inflammation and infection compared to prior methods and devices. Artificial corneas provide advantages over donor corneas including worldwide tissue availability, rapid rehabilitation for visual recovery after surgery, better visual acuity by eliminating astigmatism, a cost advantage by eliminating the need for human corneal tissue preservation, and, significantly, elimination of the risk of transmittable infectious diseases from the donor, such as hepatitis, syphilis, human immunodeficiency viral disease (HIV), and Creutzfeldt-Jacob disease (CJD).

The multi-phase artificial corneal implants embodying features of the invention thus offer many advantages while performing their main purpose of giving sight to millions of people who are blind due to corneal diseases. The devices and methods are further applicable to artificial implants of other organs, and are useful in bioengineering fields related to artificial tissues and organs.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

Figure 1:
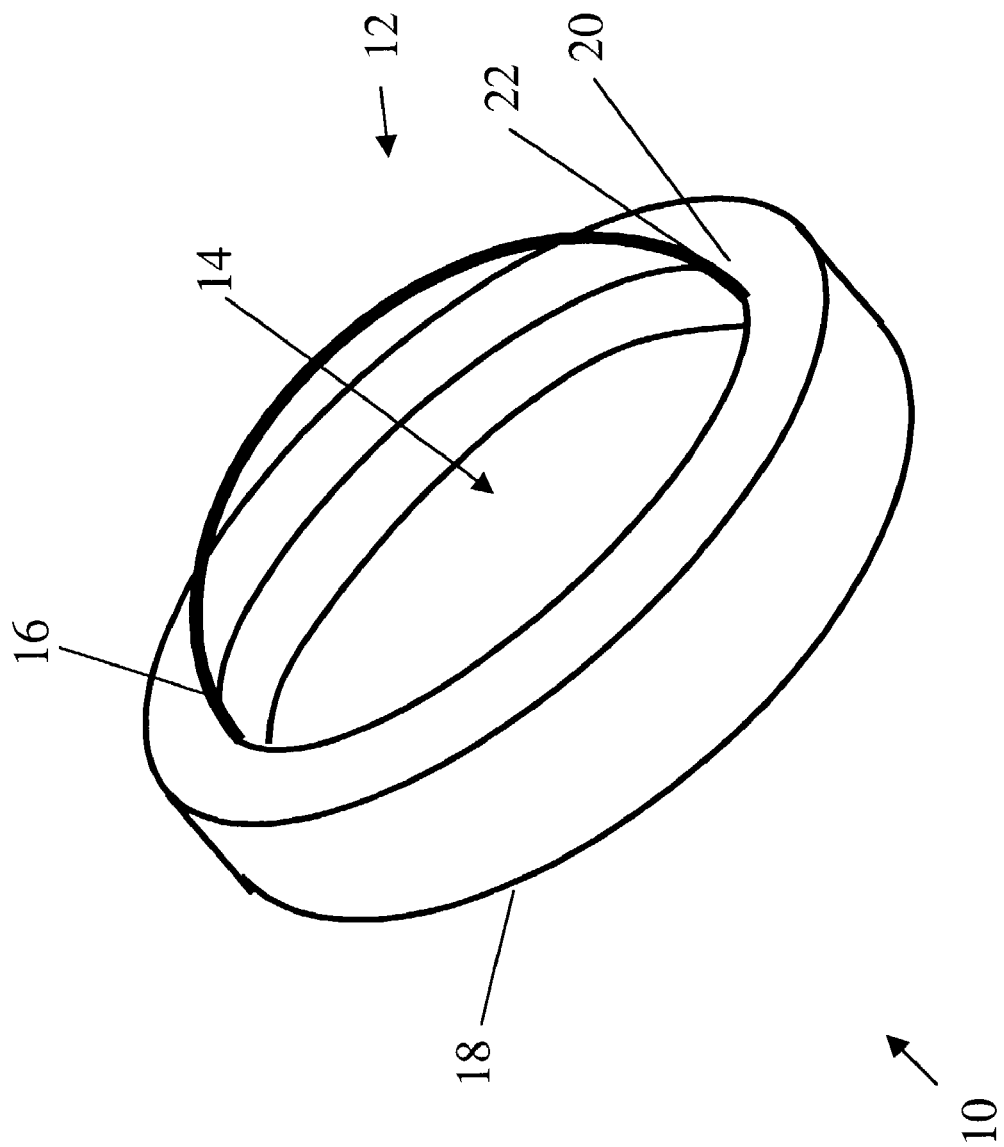
FIG. 1 shows a schematic diagram of an artificial cornea embodying features of the invention showing a core/porous skirt construct ready to be sutured onto an eye as a corneal implant.

FIG. 1 shows a schematic diagram of an artificial cornea 10 embodying features of the invention including a core/skirt construct 12 ready to be sutured onto the eye as a corneal implant. The core/skirt construct 12 has a central core 14 and skirt 18 joined at a core/skirt interface 22. The core 14, which has a core periphery 16, and skirt 18 having a skirt periphery 20 are securely attached by interface 22, which joins together the core periphery 16 with a skirt perphery 20. Skirt 18 is preferably a porous skirt. Such an artificial cornea 10 may be implanted by techniques similar to those used for penetrating keratoplasty and for the implantation of other forms of corneal prostheses (see, e.g., Trinkaus-Randall, "Cornea", Ch.35 in Principles of Tissue Engineering, 2nd ed., Academic Press (2000)).

The methods of modern chemistry may be used to attach new types of skirts 18 (incorporating a wide range of biocompatible materials) to a core 10 that include a flexible transparent material. A central core 14 of an artificial cornea 10 embodying features of the invention is preferably configured to promote the growth of epithelial cells over its surface. A skirt 18 is preferably configured to be hydrophilic and porous, effective to promote the growth of keratocytes and blood vessels. An artificial cornea 10 embodying features of the invention is mechanically strong, having a robust core/skirt interface 22. An artificial cornea 10 embodying features of the invention may include a two-phase structure, or may include a three-phase structure. A two-phase structure includes a central optical core 14 made from, for example, poly(2-hydroxyethyl methylacrylate) (pHEMA), and a skirt 18 made from, for example, collagen in a polymer matrix (e.g., polytetrafluoroethylene (PTFE)). A three-phase structure includes, in addition to a central optical core 14 and a skirt 18, a core/skirt interface 22.

Figure 2:
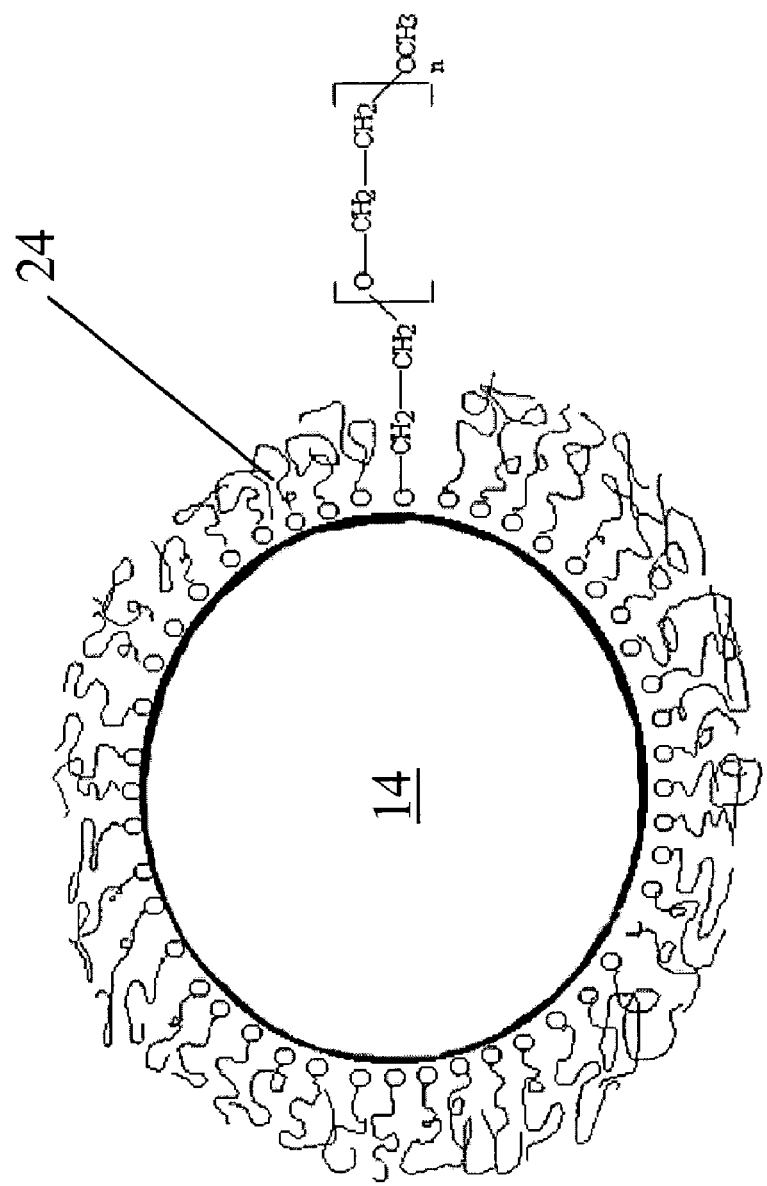
FIG. 2 shows a schematic diagram of a polymer brush attached to the central optic core of an an artificial cornea embodying features of the invention.

The synthesis of both two- and three-phase systems is used in artificial corneas 10 having features of the invention. A two-phase system involves the direct chemical coupling of a peripheral rim (skirt 18) to the periphery of a central optical region (core 14). A three-phase system involves the synthesis of a short water-soluble polymer "linker" brush 24 onto the periphery of the core 14, and subsequent attachment of the skirt 18 to the polymer brush 24. The core/skirt interface 22 between core periphery 16 and skirt periphery 20 thus includes polymer brush 24 in a three-phase system. FIG. 2 presents a schematic diagram illustrating a polymer brush 24. The choice of a two- or three-phase system will depend on the chemical reaction schemes for coupling specific biocompatible core and skirt materials.

The hydrogel core 14 of an artificial cornea 10 having features of the invention is a surrogate for the stroma, the major structural component of the cornea. The stroma is composed of an extracellular matrix rich in collagen and sulfonated proteoglycans. The skirt 18 of an artificial cornea 10 having features of the invention is preferably composed of a biocompatible material similar to the stroma in order to anchor the artificial cornea to the eye. The use of collagen in an interpenetrating biocompatible polymer network is effective to anchor the artificial cornea to the eye. The secure attachment of collagen to the core 14 is important, in order to prevent separation after implantation. Collagen may be attached to a core 14 of an artificial cornea 10 embodying features of the invention in any suitable manner, including in either of the two ways discussed infra.

Each phase making up an artificial cornea embodying features of the invention is preferably a homogeneous phase. For example, a clear central core 14 may preferably be a homogenous phase of, for example, pHEMA, or a homogenous phase comprised of pHEMA coated with collagen. A skirt 18 may be a homogenous phase comprised of, for example, collagen in a PTFE matrix. A polymer brush linker region may be comprised of a homogenous phase of, for example, polyethylene glycol (PEG).

In a first method for attaching collagen to a hydrogel core 14, the periphery 16 of the core 14 can be functionalized so as to chemically bond the collagen skirt 18 and skirt periphery 20 directly to the core via the amino or carboxyl groups on the collagen. Since the collagen fibrils themselves are rather stiff, interweaving the collagen fibrils with a more flexible biocompatible polymer network, which can be covalently attached to the hydrogel core, can facilitate the formation of a regular porous skirt. This network could be a spongy hydrogel such as pHEMA or some other biocompatible polymer, such as a copolymer of acrylonitrile and an olefinically unsaturated comonomer bearing anionic groups. This provides a two-phase artificial cornea.

A second method for attaching a skirt 18 to a core 14 is to use a water-soluble polymer brush 24 as an intermediate coupling layer between the central optic core 14 and the skirt material 18, shown in FIG. 2. This has the advantage of offering more options for attaching a collagen skirt to the core, if covalent attachment does not result in a secure physical structure because of insufficient covalent bonding to form a strong interface. Another potential advantage is that the polymer brush could be extended to form a regular polymer matrix, which would interpenetrate the stiffer and possibly more irregular collagen matrix. This second method provides a three-phase artificial cornea.

Materials that can be used need to address the various biocompatibility, peripheral host-keratocyte adhesion, mechanical strength and clinical requirements. Advances in polymer chemistry in the last few years have made the covalent attachment of two or more different materials to form a robust, secure joint a routine process. An example is the formation of a 'polymer brush', which includes polymer dangling into the solvent (water) with one end bonded to a surface. The attachment can be made by the chemical end-grafting of a water soluble homopolymer (composed of identical monomer units), or by the adsorption of one of the blocks of a diblock copolymer (each 'block' is like a homopolymer, with the two 'blocks' joined at a single junction). The properties of the water-soluble brush, including its thickness and density profile depend on the molecular weight, polymer coverage, amount of hydration, and the nature of the surface.

FIG. 2 is a greatly exaggerated schematic diagram of a polymer brush attached to the central optic core of an artificial cornea embodying features of the invention. The polymer shown is PEG, which is known to inhibit the nonspecific, noncovalent surface adsorption of proteins (Kim et al., "Effect of Poly(ethylene glycol) Graft Polymerization of Poly(methyl methacrylate) on Cell Adhesion", J. Cataract Refract. Surg., 27, 766–774 (2001)). A polymer brush can be used to couple a biocompatible skirt material to the core.

Figure 3:
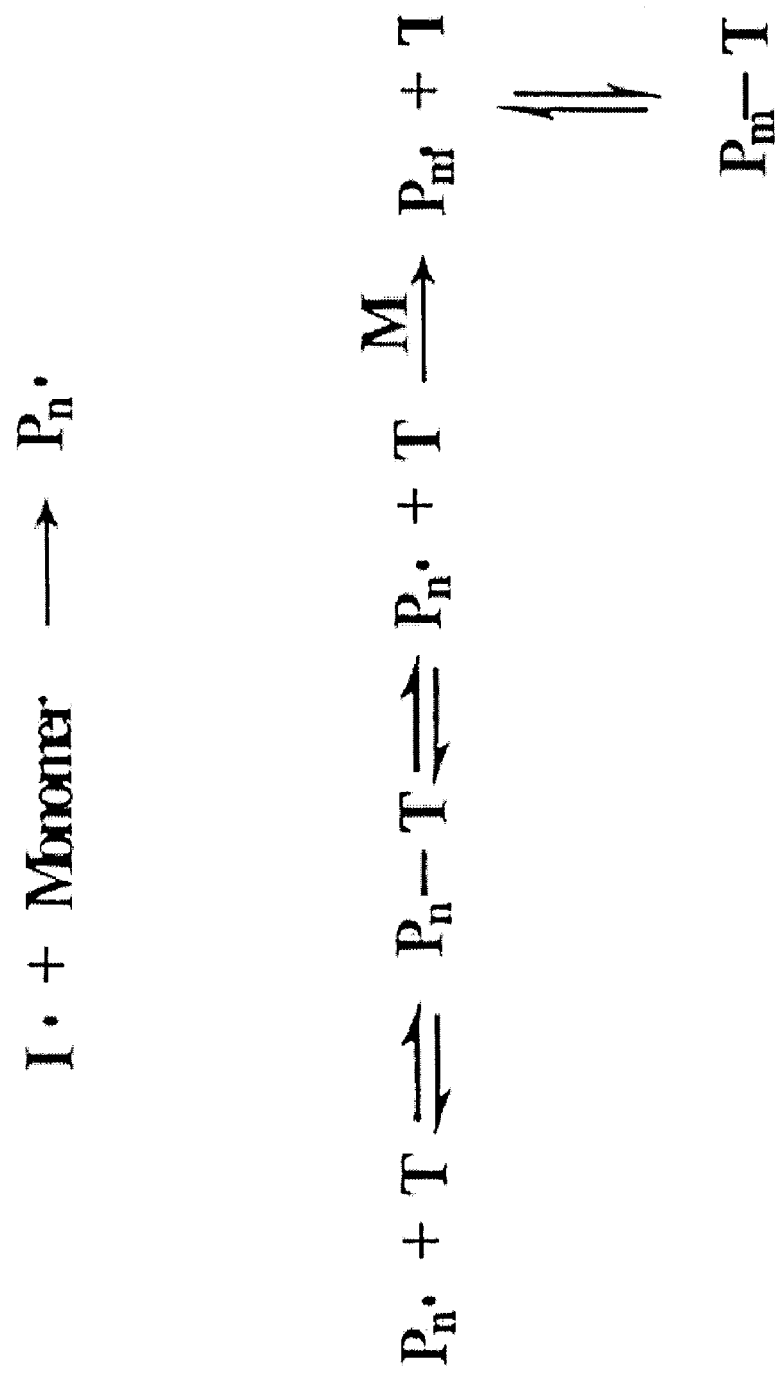
FIG. 3 shows a general reaction scheme for living-radical polymerizations useful for producing well-defined water-soluble polymers.

Well-defined water-soluble polymers can be produced by a technique called living free radical polymerization, which is currently an active and rapidly developing field of polymer science. Living-radical polymerizations are essentially conventional radical polymerizations performed in the presence of some species that react reversibly with the propagating chains (See e.g. Hawker, "Accurate Structural Control and Block Formation in the Living Polymerization of 1,3-Dienes by Nitroxide-Mediated Procedures", Macromolecules 33, 363-370 (2000)). The general chemistry of a living-radical polymerization process is shown in FIG. 3, which presents the general reaction scheme for living-radical polymerizations. Such reactions are useful for producing well-defined water-soluble polymers.

As shown in FIG. 3, after initiation, a propagating radical chain, (Pn.), will either add monomer, (M), and continue to grow, or react with a reversible capping species, T, to form a dormant chain, (Pn-T). At any given time, most of the polymer chains are in the dormant form and the concentration of the active chains is low enough ($10^{-6}$ M) that the probability of two chains colliding with each other and terminating is dramatically reduced. Although some termination continues to occur throughout the course of the polymerization, the amount decreases progressively as the polymerization proceeds since termination by coupling generally involves at least one very short chain. Under appropriate conditions, typically elevated temperatures, the dormant species reacts to generate a propagating radical chain and the species T. The reversible terminating species T then competes with monomer to add to the propagating chain. Narrow polydispersity resins are obtained when the equilibrium between the active and dormant chains is fast. The persistent radical effect ensures that a steady concentration of active radicals exist to enable the polymerization to proceed at an acceptable rate. An example of a water-soluble polymer currently under investigation using stable free radical polymerization is polyacrylonitrile.

Different materials may be used for the core in building two- and three-phase core/skirt keratoprosthesis. In addition, the inclusion of cell growth factors, antibiotics, and other biologically active substances into the skirt, either as molecular entities, or in time-release micro- or nano-capsules embedded in the skirt may enhance the desired growth of cells and reduce inflammation or other undesirable reactions to implantation of an artificial cornea.

Polymethylmethacrylate (PMMA) has been used as an optically clear material for the core of many keraprosthesis designs, since it is biologically inert, transparent, easy to fabricate, and can be manufactured to a broad range of optical powers (See e.g. Kirkham, et al., "The Keratoprosthesis: Improved Biocompatibility Through Design and Surface Modification", Ophthalmic Surgery, 22, 455–461 (1991)). However, tissue melt (an enzymatic process involving proteolytic enzymes such as collagenases) and tissue necrosis has often occurred at the junction of the hard PMMA core and biological tissue, leading to aqueous leak and infection. This may be due to the rigidity of the PMMA, which is likely to cause dynamic stress during the constant motion of the eye encountered in vivo. To reduce the rigidity of the artificial cornea and to reduce the risk of inflammation, tissue melt, tissue necrosis, and other possible problems, other materials more flexible than PMMA, such as silicone and hydrophilic acrylics (such as are used as intraocular lenses) may be used for the core of the keraprosthesis.

A phase or phases making up an artificial cornea embodying features of the invention may be cross-linked and may contain pores. Cross-linking materials used in an artificial cornea embodying features of the invention helps to reduce long-term swelling of the material, and provides a distribution of pores of various sizes which may be helpful in promoting cellular attachment and growth. Cross-linking of materials making up an artificial cornea may be performed by any suitable means, including by exposure to ultraviolet radiation, by application of cross-linking agents such as, for example, glutaraldehyde or formaldehyde, or by other means or method. Preferably, a phase including pores has a relatively small pore size (in comparison with respect to the size of corneal cells) and a narrow distribution of pore sizes. A material having a narrow distribution of pore sizes (e.g., a material in which pores have sizes varying mostly within a range of about ten-fold) is preferred and provides an artificial cornea more readily accepted by a recipient eye than one including materials having a much wider distribution of pore sizes. However, a material having a wide distribution of pore sizes (e.g., a distribution in which pore sizes vary by more than about twenty-fold or more), is not preferred.

An artificial cornea embodying featuers of the invention may contain or may be coated with biologically-active substances, including, for example, growth factors, cytokines, antibiotics, or other drugs or hormones. For example, coating an artificial cornea with a layer of collagen may improve its performance and reduce the risk of rejection. Similarly, an artificial cornea may be coated with growth factors or other biologically active materials. Growth of corneal epithelial cells over an artificial cornea improves its performance and reduces the risk of rejection; such overgrowth may be promoted by, for example, growth factors, cytokines, antibiotics, or other biologically-active substances. Corneal epithelial cells may be induced to overgrow an artificial cornea before implantation in a recipient eye, after implantation in a receipient eye, or both.

There are several ways to add cell growth factors, antibiotics, and other biologically-active substances to the skirt material. One technique is to use covalent linkage to GPI (glycolsyl-phosphatidylinositol) anchors in order to attach the proteins involved in cell growth to the collagen matrix. The covalent linkage of growth factors to GPI molecules is recognized as an important mechanism for anchoring them to cell membranes and to other substrates (See e.g. Low, M. G., "Glycosyl-phosphatidylinositol: a Versatile Anchor for Cell Surface Proteins", The FASEB Journal, 3, 1600–1608 (1989). Another way to incorporate growth factors and/or antibiotics into the skirt material is to use polymeric drug delivery through micro- or nano-sized particles (See e.g. Fu, et al., "Protein Stability in Controlled Release Systems", Nature Biotechnology, 18, 24–25 (2000)) embedded into the skirt matrix. Drug molecules encapsulated in a polymer shell can be released through a hole created by a chemical or enzymatic event. The drug molecules may also be embedded in the polymer and diffuse out on their own or due to degradation of the polymer. For example, this mechanism can be used to deliver collagenase inhibitors, such as topical 1% medroxyprogesterone, which is effective in reducing gelatinase and collagenase synthesis as well retarding corneal ulceration in animals, and a 1% tetracycline solution, which is a potent direct enzyme inhibitor. As another example, it has recently been discovered that thymosin beta4 is a potent healing factor, particularly for corneal epithelial cells (See e.g. Malinda et al., "Thymosin β4 Accelerates Wound Healing" Journal of Investigative Dermatology, 113, 364–368 (1999)). Thus, collagenase inhibitors, such as topical 1% medroxyprogesterone, 1% tetracycline solution, thymosin beta4 and other drugs, such as other drugs used in postoperative management to reduce complications following keraprosthesis surgery, are suitable for inclusion in artificial corneas embodying features of the invention.

Techniques used in the fields of surface science, such as microfabrication technology, may be applied to artificial corneas to provide surfaces configured to encourage tissue integration both for cellular penetration into the peripheral skirt and for epithelial cell coverage over the surface of the keratoprosthesis. Surface science and microfabrication techniques may be used in conjunction with chemical strategies to create a well-defined and controlled interface between the skirt and core. Different surface modification protocols for attaching biocompatible materials (such as collagen) to the surface of the keratoprosthesis may be used to promote epithelial cell growth. For example, techniques as discussed in e.g. Desai et al., "Nanopore Technology for Biomedical Applications", Biomedical Microdevices, 2, 11–40 (1999) may be used to prepare surfaces of artificial corneas.

Parts of the central optic core can be masked and exposed surfaces can be chemically treated to allow bonding of other materials to the core. There are several ways of achieving this. Generally the surface to be treated is immersed in an aqueous dispersion of a polymerizable surfactant, a cross-linking agent, and a free radical initiator. The surface is then exposed to ultraviolet light to form a permanent cross-linked surface coating (See e.g. Valint, "Surface Coating of Polymer Objects", U.S. Pat. No. 5,135,297). Both the surface of the core and its periphery can be treated in this way. Collagen-coated surfaces may be used to prepare the surface of an artificial cornea in order to inhibit bacterial adherence or reduce platelet deposition to an artificial cornea (see, e.g., McGrady et al., "Specific and Charge Interactions Mediate Collagen Recognition by Oral Lactobacilli", J. Dent. Res., 74, 649–657 (1995); Abulencia et al., "Comparative Antiplatelet Efficacy of a Novel, Nonpeptide GPIIb/IIIa Antagonist (XV454) and Adciximab (c7E3) in Flow Models of Thrombosis", Arterioscler. Thromb. Vasc. Biol., 21, 149–156 (2001)). Different types of animal collagen, and autologous collagen from the stroma of the patient in the peripheral skirt may be used to increase the biocompatibility and further improve the tolerance of the keratoprosthesis in vivo.

Such collagen coating is effective to promote activity supportive of cellular growth onto an artificial cornea. Other treatments, such as treatment of artificial corneas with type 1 collagen, with poly(vinyl alcohol) copolymer coated with collagen type I, and with copolymers of hydroxyethyl methacrylate (HEMA) and methyl methacrylate, and with other compounds and mixtures, may be effective to promote epithelial adherence to the artificial cornea and to promote cellular proliferation effective to aid in tolerance of the implant in a patient (see, e.g., Kirkham et al., "The Keratoprosthesis: Improved Biocompatibility Through Design and Surface Modification", Ophthalmic Surgery, 22, 455–461 (1991)).

Peptide, protein, and cellular interactions with self-assembled monolayer model surfaces can be prepared having a range of oxidation states by employing —$CF_3$, —$CH_3$, —$CO_2CH_3$, and —$CH_2OH$ terminal functionalities (See e.g. Margel et al., "Peptide, Protein, and Cellular Interactions With Self-Assembled Monolayer Model Surfaces" J. Biomed. Mater. Res., 27, 1463–1476 (1993)). Amino groups on the surface of a polymeric material can be deprotected by acid hydrolysis (See e.g. Zheng et al., "Modification of Materials Formed From Poly(L-lactic acid) to Enable Covalent Binding of Biopolymers: Application to High-Density Three-Dimensional Cell Culture in Foams With Attached Collagen" In Vitro Cell Dev. Biol. Anim., 34, 679–684 (1998)). Collagen can then be covalently linked to the deprotected amino groups, creating a surface capable of high-density cell growth. In this way one can encourage epithelial cell growth on some synthetic polymeric biomaterials, such as polyesters (See e.g. Tjia et al., "Substrate-Absorbed Collagen and Cell Secreted Fibronectin Concertedly Induce Cell Migration on Poly(lactide-glycolide) Substrates", Biomaterials, 20, 2223–2233 (1999)). It is now well accepted that the attachment of proteins to polymeric surfaces affects the performance of the composite material, and that the performance can be optimized by the appropriate design of the interface. Methods for the design of polymeric biomaterials with low bacterial attachment and associated inhibition of biomaterial-associated infections are discussed in e.g. Montdargent et al., "Toward New Biomaterials" Infect. Control Hosp. Epidemiol., 21, 404–410 (2000).

Such modifications suitable for attaching biologically-active substances to an artificial cornea may be used to attach any desired biologically-active substance, such as, for example, anitbiotic molecules. Antibiotics suitable for incorporation into artificial corneal implants embodying features of the invention include penicillins, ampicillins, amoxicillins, cephalosporins, vancomycins, aminoglycosides, quinolones, polymyxins, erythromycins, tetracyclines, streptomycins, sulfa drugs, chloramphenicols, clindamycins, lincomycins, sulfonamides, ceftiofur crystalline free acid, ceftiofur hydrochloride, tylosin, tilmicosin, chloramphenicol, florfenicol, tobramycin, gentamycin, bacitracin, neomycin, polymyxin, gramicidin, naphthyridine, and erythromycin; tetracyclines such as tetracycline, oxytetracycline, chlortetracycline, oxytetracycline; fluoroquinolone derivatives including enrofloxacin, danofloxacin, premafloxacin, norfloxacin, ofloxacin, and ciprofloxacin; antibacterials such as sulfonamides, sulfacetamide, sulfamethizole and sulfisoxazole; other antibacterial agents such as nitrofurazone and sodium propionate; and antivirals, including idoxuridine, and analogs, derivatives and salts of these compounds.

Growth factors, growth promoters, growth inhibitors, adhesion molecules, cytokines, and hormones may also be incorporated into artificial corneas embodying features of the invention. Growth factors and cytokines suitable for incorporation into artificial corneal implants embodying features of the invention include epidermal growth factor (EGF), fibroblast growth factor (FGF), granulocyte colony stimulating factor (G-CSF), granulocyte-macrophage colony stimulating factor (GM-CSF), Nerve Growth Factor (NGF); Insulin-like Growth Factor (IGF, such as IGF-I and IGF-II); Platelet Derived Growth Factor (PDGF), Fibroblast Growth Factors (FGF) including acidic and basic fibroblast growth factors (AFGF, bFGF), Hepatocyte Growth Factor (HGF), Transforming Growth Factors, such as Transforming Growth Factor alpha (TGF-alpha) and and Transforming Growth Factor-Beta (TG-FBeta), epidermal growth factor (EGF), connective tissue growth factor (CTGF), interleukins, interferons, pleitrophin (PTN), leukemia inhibitory factor, colony-stimulating factor-1 (CSF-1), Vascular endothelial growth factor (VEGF), ciliary neuronotrophic factor (CNTF), motor nerve growth factor (MNGF), and forskolin. Hormones suitable for incorporation into artificial corneal implants embodying features of the invention include estrogen, testosterone, thyroid hormone, corticotropin, prolactin, erythropoietin, and insulin.

Biocompatibility is an important factor in the design of a keraprosthesis to minimize postoperative complications. The physical and chemical properties of the material, typically a polymer, use to make an artificial cornea is an important factor in determining the biocompatibility of an artificial cornea. For example, polymer pore size is an important factor for tissue integration (See e.g. Trinkaus-Randall V. et al. "In vivo fiboplasia of a porous polymer in a cornea." Invest Ophthalmol Vis Sci 32, 3245–51 (1991); Trinkauss-Randall V, et al. "In vitro evaluation of fibroplasias in a porous polymer." Invest Ophthalmol Vis Sci 31, 1321–6 (1990)). Several different polymers used for the skirt have been tested in animals for biocompatibility, including polytetrafluoroethylene (PTFE) (trade names Proplast, Gore-Tex) and expanded polytetrafluoroethylene (ePTFE). Among these materials, ePTFE is preferred (see, e.g., Legeais et al. "A second generation of biointegrable keratoprosthesis. First in vivo evaluation" (abstract). Invest Ophthalmol Vis Sci 37 (suppl) 37, 1450 (1996); Legeais et al., "Advances in artificial corneas" (abstract). Invest Ophthalmol Vis Sci 37 (suppl) 36, 1466 (1995)). Alternatively, a carbon fiber skirt, a polypropylene/polybutylene copolymer skirt, poly(2-hydroxyethyl methacrylate) (pHEMA) or other materials can provide good tissue integration (see, e.g., Kain "The develoment of the silicone-carbon keratoprosthesis. Refract Corneal Surg 9, 209–10 (1993); Trinkaus-Randall et al. "In vitro fibroplasias of aporous polymer in the cornea." Invest Ophthalmol Vis Sci 32, 3245–3251 (1991); Chirila T V, Constable I J, Crawford G J, et al: Poly(2-hydroxyethy methacrylate) spoges as implant materials: in vivo and in vtro evaluation of cellular invasion." Biomaterials 14, 26–38 (1993)).

Polymer performance may be tested in vitro with tissue cultures and in vivo to determine the level of cellular invasion into the pores of the polymer and to determine preferred polymer materials. In addition, the effects of added substances, such as growth factors, antibiotics, and anti-inflammatory medications (such as methyl-prednislone), may be assessed by use of such animal models. For example, a method of measuring the biocompatibility of an artificial cornea implant, including a method for testing candidate keratoprosthesis materials, includes inserting the implant or material to be tested into the cornea in vivo in an animal model to assess for the level of inflammation and the rate of extrusion, and monitoring the level of tissue integration, inflammation, and complications such as tissue necrosis and extrusion. Additional modifications of the keraprosthesis may be made to encourage epithelial cell growth and tissue integration, including coating and microfabrication of the surface to allow for epithelial migration, inclusion of growth factors and growth promoters. The effects of such treatments and modifications may be determined by the same assays, including, for example, animal models for assessing the level of inflammation and cellular infiltration. In addition, the level of postoperative inflammation will be controlled by the amount of and antibiotics placed within the keraprosthesis. Again, the level of inflammation will be assessed in an animal model.

For example, poly(vinyl alcohol) copolymer coated with collagen type I is known to promote epithelial adherence and proliferation (See e.g. Trinkauss-Randall et al. "Development of a biopolymeric kertoprosthetic material." Invest Ophthalmol Vis Sci 29, 393–400 (1988)). Other polymers that support epithelial cell growth include copolymers of hydroxyethyl methacrylate (HEMA) and methyl methacrylate (MMA) (See e.g. Hicks et al., Keratoprosthesis: "Advancing toward a true artificial cornea." Survey of Ophthalmology 42, 175–189 (1997)).

Figure 4:
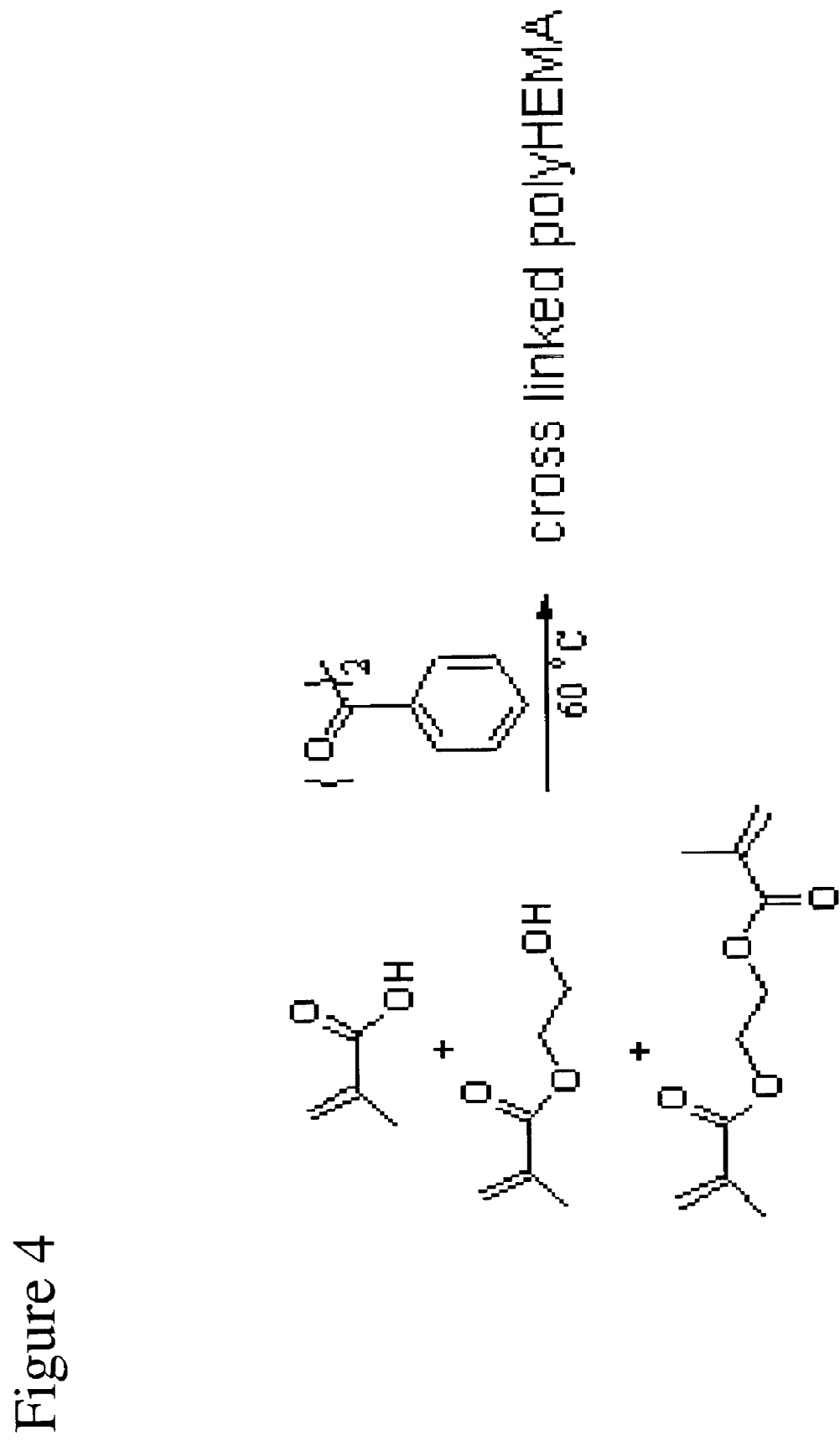
FIG. 4 shows synthesis of a cross-linked pHEMA hydrogel embodying features of the invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, surface-modified biocompatible materials could be developed to promote epithelialization and tissue integration at one site of the material (preferably the anterior site of the material). The surface modification of e.g. pHEMA hydrogels could be established via a variety of chemical methods. A preferred method is either, but not limited to, the TEMPO/bleach oxidation of pHEMA thus yielding surface aldehydes (TEMPO=2,2,6,6-tetramethyl-1-piperidinyloxy, free radical). These oxidation techniques were applied to the surface-modification of synthesized-pHEMAs hydrogel lenses (e.g. synthesized within our laboratories with a composition of 6% methacrylic acid, 93% HEMA=2-hydroxyethyl methacrylate, and ~1% EGDMA=ethyleneglycol dimethacrylate as shown in FIG. 4) and with commercially available Vifilcon-A® contact lenses (American Optical, 55% water, principal constituents: HEMA and PVP=poly(vinyl pyrrolidone)).

Figure 5:
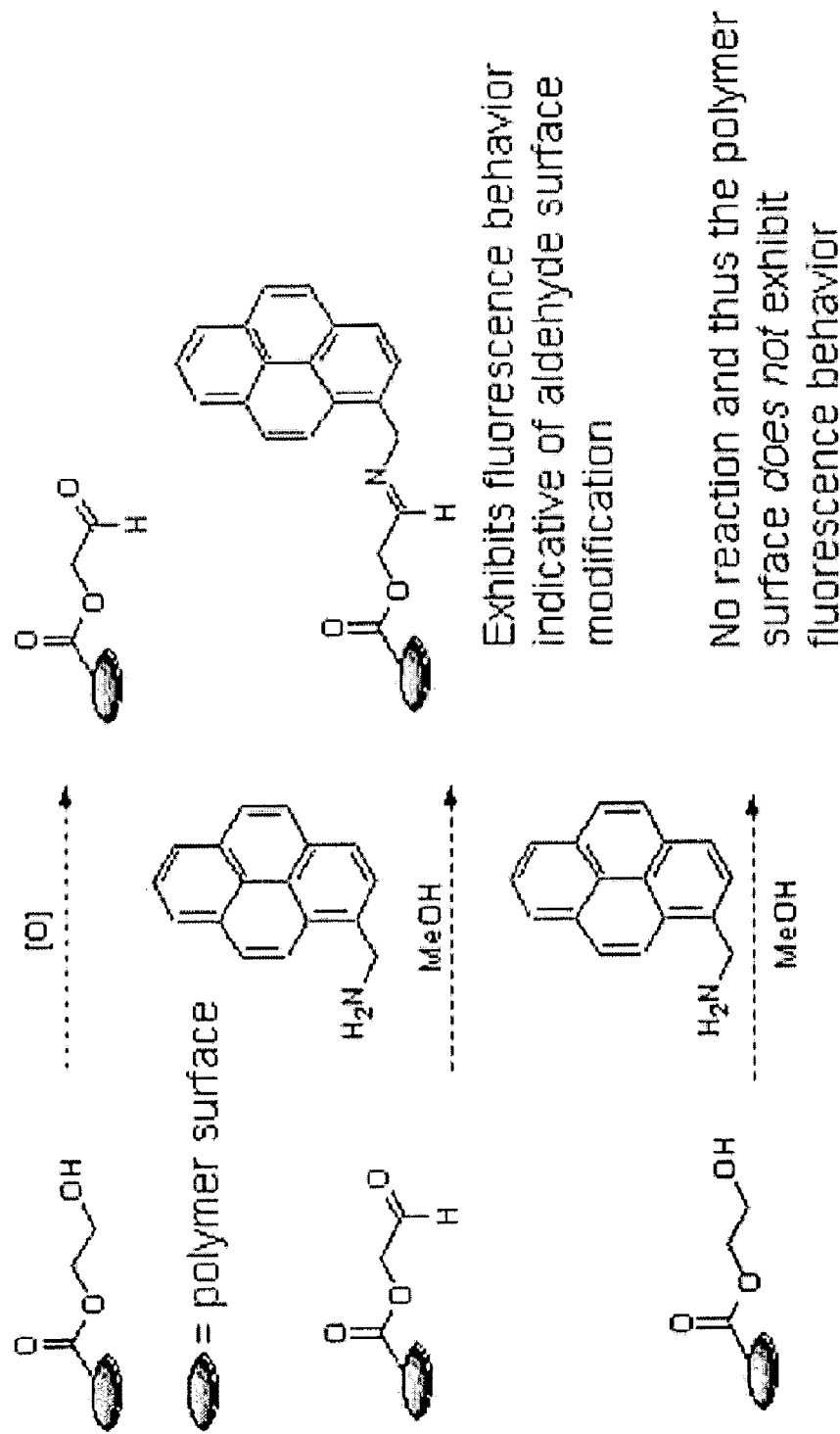
FIG. 5 shows a schematic description embodying features of the invention for the surface-oxidation of hydrogels (synthesized-pHEMAs and Vifilcon-A®) from primary alcohols into aldehydes.

To assure that surface modification was achieved, both of these "surface-modified" hydrogel lenses were treated with 1-pyrenemethylamine thus generating pyrene-imine-modified hydrogels as shown in FIG. 5. After vigorous rinsing, these compounds displayed fluorescence under UV light, which is indicative of surface modification. As shown in FIG. 5, schematic description for the surface-oxidation of hydrogels (synthesized-pHEMAs and Vifilcon-A®) from primary alcohols into aldehydes. Subsequent condensation with fluorescent 1-pyrenemethylamine generated pyrene-imine modified hydrogels. Note that non-reacted hydrogels bearing terminal alcohols (synthesized-pHEMAs and Vifilcon-A®) did not react with 1-pyrenemethylamine and thus did not fluoresce.

The goal of these surface modification strategies was to generate a hydrogel with a propensity to promote in vivo epithelialization. Toward this goal, we have investigated the two types of surface-modified hydrogel lenses (synthesized-pHEMAs and Vifilcon-A®) for surgical implantation into bovine organ culture model eyes. In all cases, the surface-modified hydrogels were found to promote in vivo epithelialization while the non-surface-modified hydrogels did not. The histological investigations of these surgical implants demonstrated a cell layer of epithelium covering the modified pHEMA, which is covalently bonded with collagen.

The surface modification of pHEMAs could be extended to the generation of carboxyl substituents. Chemical techniques including oxidative ester cleavage with $BCl_3$ or oxidation of the terminal alcohols with $KMNO_4$ or $Ag_2O$ could be used. The use of plasma-deposition as an alternative technique for the development of these surface functionalities could also be used. These carboxyl substituents could be covalently linked with collagen to form amide linkages via typical dicyclohexylcarbodiimide-mediated coupling.

All such variations are considered to be within the scope and spirit of the present invention as defined by the following claims and their legal equivalents.

What is claimed is:

1. An artificial cornea comprising:
   (a) a first phase comprising a biocompatible, optically clear central core having anterior and posterior surfaces, and a perimeter; and
   (b) a second phase comprising a biocompatible, hydrophilic, porous skirt surrounding and covalently linked to said perimeter of said central core, wherein said skirt comprises a polytetrafluoroethylene (PTFE) matrix containing collagen or an expanded polytetrafluoroethylene (ePTFE) matrix containing collagen.

2. The artificial cornea as set forth in claim 1, further configured to promote the growth of epithelial cells over said anterior surface.

3. The artificial cornea of claim 1, wherein said central core comprises poly(2hydroxyethyl methylacrylate).

4. The artificial cornea of claim 1, wherein said core comprises a soft biocompatible material used for making intraocular lenses.

5. The artificial cornea of claim 4, wherein said soft biocompatible material is selected from the group consisting of silicone, silicone compounds and hydrophilic acrylics.

6. The artificial cornea of claim 1, further comprising a biologically-active substance selected from the group consisting of growth factors, growth promoters, growth inhibitors, hormones, antibiotics and adhesion molecules.

7. An artificial cornea comprising:
  (a) a first phase comprising a biocompatible, optically clear central core having anterior and posterior surfaces, and a perimeter;
  (b) a second phase comprising a biocompatible, hydrophilic, porous skirt surrounding said perimeter of said central core; and
  (c) a third phase comprising a polymer brush at an interface region disposed between said core and said skirt, and covalently connected to said perimeter of said central core and covalently connected to said skirt.

8. The artificial cornea of claim 7, further configured to promote the growth of epithelial cells over said anterior surface.

9. The artificial cornea of claim 7, wherein said skirt comprises a polytetrafluoroethylene (PTFE) or an expanded polytetrafluoroethylene (ePTFE) matrix containing collagen.

10. The artificial cornea of claim 7, wherein said polymer brush comprises a hydrophilic polymer polymerized by methods including living radical polymerization.

11. The artificial cornea of claim 7, wherein said core comprises a soft biocompatible material used for making intraocular lenses.

12. The artificial cornea of claim 11, wherein said soft biocompatible material is selected from the group consisting of silicone, silicone compounds and hydrophilic acrylics.

13. The artificial cornea of claim 7, further comprising a biologically-active substance selected from the group consisting of growth factors, growth promoters, growth inhibitors, hormones, antibiotics and adhesion molecules.

14. An artificial cornea comprising:
  (a) a first phase comprising a biocompatible, optically clear central core having anterior and posterior surfaces, and a perimeter, wherein said central core comprises poly(2hydroxyethyl methylacrylate) and wherein one surface of said poly(2hydroxyethyl methylacrylate) is chemically modified to promote epithelialization.
  (b) a second phase comprising a biocompatible, hydrophilic, porous skirt surrounding and covalently linked to said perimeter of said central, wherein said skirt comprises a polytetrafluoroethylene (PTFE) matrix containing collagen or an expanded polytetrafluoroethylene (ePTFE) matrix containing collagen.

* * * * *